US010426413B2

(12) United States Patent
Rusin et al.

(10) Patent No.: US 10,426,413 B2
(45) Date of Patent: *Oct. 1, 2019

(54) PATIENT ALARM DATA APPLICATION

(71) Applicant: Medical Informatics Corporation, Houston, TX (US)

(72) Inventors: Craig Rusin, Houston, TX (US); Emma Fauss, Houston, TX (US)

(73) Assignee: Medical Informatics Corp., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,510

(22) Filed: Apr. 2, 2019

(65) Prior Publication Data

US 2019/0223811 A1      Jul. 25, 2019

Related U.S. Application Data (63) Continuation of application No. 14/947,824, filed on Nov. 20, 2015, now Pat. No. 10,271,799.

(60) Provisional application No. 62/082,984, filed on Nov. 21, 2014.

(51) Int. Cl.
*G08B 23/00*      (2006.01)
*A61B 5/00*      (2006.01)

(52) U.S. Cl.
CPC ............ *A61B 5/746* (2013.01); *A61B 5/0022* (2013.01); *A61B 5/7435* (2013.01)

(58) Field of Classification Search
CPC ... A61B 5/7221; A61B 5/1118; A61B 5/7282; A61B 5/0402; A61B 5/14532; A61B 5/02055; A61B 5/02405; A61B 5/0022; A61B 5/4266; A61B 5/1116; A61B 5/14542; A61B 5/021; A61B 5/0488; A61B 5/0816; A61B 5/0476
USPC ....................................................... 340/573.1
See application file for complete search history.

(56) References Cited

U.S. PATENT DOCUMENTS

| 10,271,799 B2 * | 4/2019 | Rusin .................. A61B 5/0022 |
| 2015/0051462 A1 | 2/2015 | Olsen |
| 2016/0321904 A1 | 11/2016 | Johnson |

* cited by examiner

*Primary Examiner* — Tanmay K Shah
(74) *Attorney, Agent, or Firm* — Schafer IP Law (57) ABSTRACT

A patient alarm application provides a way for allowing clinical personnel to monitor and control patient-specific alarm settings. A user interface allows clinical personnel to compare graphical representations of unit population vital signs data with patient-specific vital signs data as well timelines of alarms for the patient. Analysis of the alarm data allows the user interface to show clinical personnel the estimated effects of changes to alarm threshold settings.

20 Claims, 5 Drawing Sheets

PATIENT ALARM DATA APPLICATION

CROSS REFERENCE TO RELATED APPLICATIONS

This Application claims priority to U.S. patent application Ser. No. 14/947,824 entitled "Patient Alarm Data Application" filed Nov. 20, 2015, which claims the benefit of U.S. Provisional Application Ser. No. 62/082,984, entitled "Patient Alarm Data Application" filed Nov. 21, 2014, all of which are incorporated by reference in their entirety herein.

TECHNICAL FIELD

The present invention relates to the field of managing alarms in a hospital setting, and in particular to techniques for understanding an alarm generation environment for a patient and evaluating the effects of different alarm thresholds.

BACKGROUND ART

Hospital Intensive Care Unit (ICU) workers are overwhelmed by alarms. Chemical and power industry standards for alarms are that one worker should be asked to respond to no more than 100-300 alarms per 8 hour shift. ICU nurses are routinely asked to respond to greater than 300 alarms in a shift (sometimes greater than 1000), the vast majority (95%) of which are false or non-critical. The Joint Commission which accredits and certifies more than 20,000 health care organizations and programs in the United States, in 2013 issued a white paper outlining the problems of alarm fatigue and declaring it a frequent and persistent problem and outlining proposals for dealing with it.

In order to evaluate any change in alarm management, it is important to be able to quantify and monitor the alarm problem. Current approaches to alarm management do not provide adequate tools for clinical personnel to understand alarm environments or evaluate patient-specific effects of changes to alarm thresholds.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims may be necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

As used herein, the term "a computer system" can refer to a single computer or a plurality of computers working together to perform the function described as being performed on or by a computer system. Similarly, as used herein, the term "machine readable medium" can refer to a single physical medium or a plurality of media that together store the information described as being stored on or by the machine readable medium.

As used here, "vital signs" is another term for physiological data associated with a patient that may be captured by a patient monitoring system. Typical vital signs or physiological data can include heart rate, respiratory rate, $SpO_2$ date, etc.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

Because conventional hospital monitoring systems are incapable of remotely monitoring all of the physiological data generated by physiological sensors attached to a patient, such monitoring systems have had limited patient alarm and physiological data available for display remote to the bedside units that may display individual sensor data. In addition, what data is captured is often provided to clinical personnel such as doctors or nurses in simple numerical form, without providing ease of use graphical features such as curves or histograms.

In addition, although clinical staff have been able to change alarm thresholds for patients, the patient monitoring systems have no assisted clinical personnel as they try to decide what alarm thresholds to use for a patient. A threshold too high might reduce the number of alarms, but might either have insufficient effect on the number of alarms to reduce the alarm overload conditions of the unit significantly or might have such an effect that medically important alarms were suppressed. Clinical care personnel such as nurses have turned off alarms that are too frequently triggering, but have not had tools to know whether doing so is either helpful or safe. Patient friends or family have been known to turn off alarms in an effort to allow a patient to sleep, without being aware of the effect that might have in the event of a deterioration of a condition of the patient. Alternately an alarm threshold too low might cause alarm floods and overload the ability of clinical personnel to respond to those alarms.

While all alarms should be responded to, they can be responded to differently. Hospital units/departments find that constant alarms not only keep nurses from responding appropriately, because there are too many to handle, but the alarms also tend to cause patient distress from all of the alarms in their area. By allowing primary alarms limits to be set to lower but still safe limits or delays, the clinician can reduce or eliminate alarm floods, improving care throughout the unit and reducing patient annoyance and sleep disruption.

A Patient Alarm Data Application provides a way to provide a patient-specific user interface that can assist clinical personnel in their understanding and decision making about alarms and alarm threshold settings.

The Patient Alarm Data Application and underlying platform allow patient-specific analytics to be calculated for an individual patient. Clinical users can assign this application to a specific patient, a program is then instantiated on that patient in a platform system, and results are calculated and then displayed through a web or other user interface to the clinical user.

Although described herein in terms of a clinical environment and clinical personnel, a similar system may be deployed in other environments, including a home monitoring environment.

Figure 1:
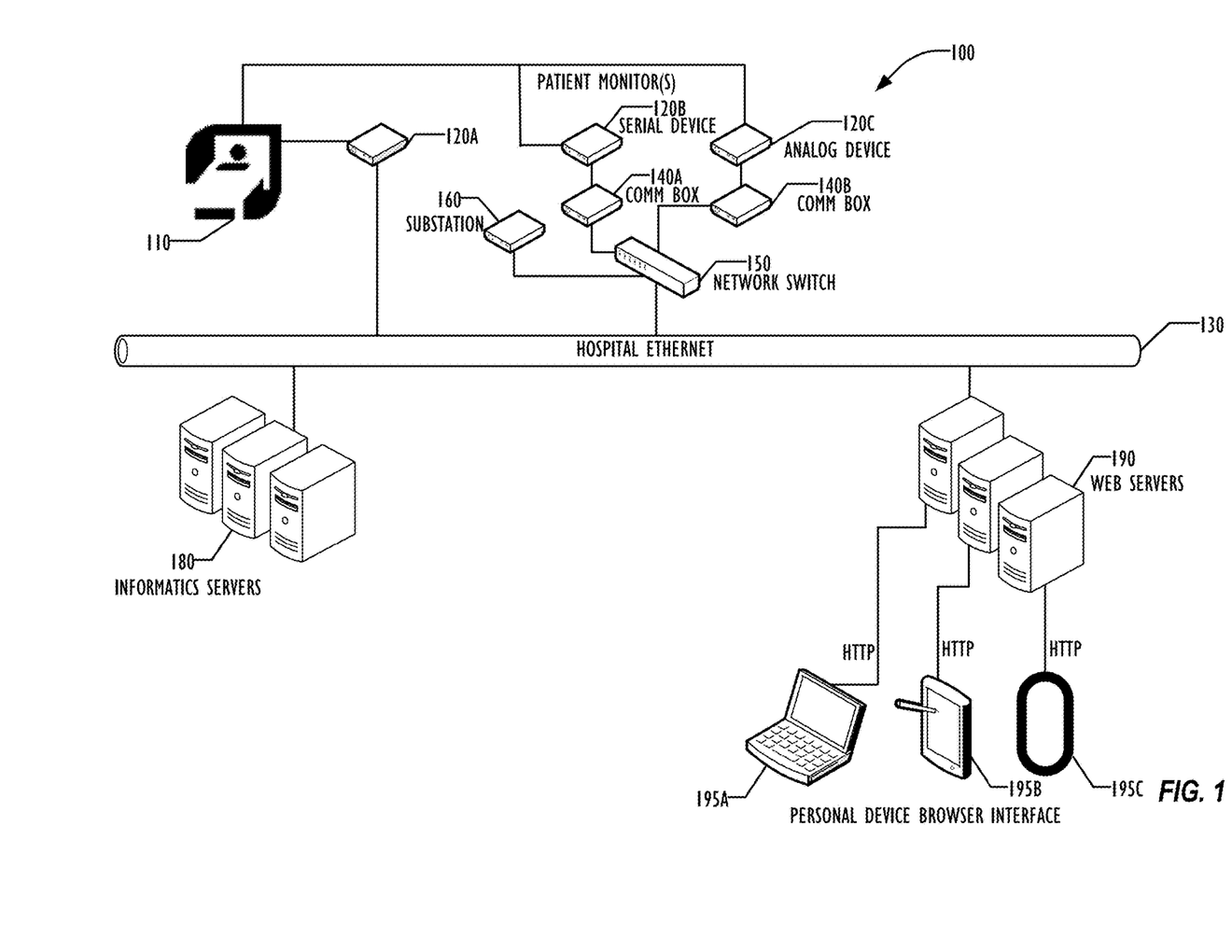
FIG. 1 is a block diagram illustrating a network of devices employed by a hospital system for an alarm management system according to one embodiment.

FIG. 1 is a block diagram illustrating a platform 100 for collecting, analyzing, and displaying alarm-related information in a healthcare environment according to one embodiment.

As illustrated, there are two types of servers: the informatics server(s) 180 and the web server(s) 190. Any number of any of the types of servers may be deployed as desired, and other servers providing other information processing functionality may be included as desired. All of the servers 180-190 connect to each other and the bedside monitors via one or more hospital networks 130. Although illustrated as a single hospital Ethernet network 130, any number of interconnected networks may be used, using any desired networking protocols and techniques.

Also connected to the hospital network 130 are a number of bedside monitors for monitoring physiological data for a patient in bed 110. These bedside monitors may include network connected monitors 120A, which can deliver digital physiological data to the hospital network 130, serial devices 120B, which produce digital data but are not directly connected to a network, and analog devices 120C, which produce analog data and are not directly connected to a network. Communication boxes 140A and 140B allow connecting the serial devices 120B and analog devices 120C, respectively, to the hospital network 130, typically through a network switch 150. In addition, a substation 160 may be also connected to the network 130 via the network switch 150 for performing data manipulation and time synchronization. Any number of bedside monitor devices 120 may be used as determined advisable by physicians and other clinical staff for the patient in bed 110.

Although as illustrated in FIG. 1 the bedside monitors and associated communication devices are connected directly or indirectly to the hospital network 130, remote bedside monitoring devices may be used as part of the system 100, such as home monitoring devices, connected to the hospital network 130 indirectly through the Internet or through other communication techniques.

The web servers 190 are configured for communicating with mobile devices such as laptop 195A, tablet 195B, or smart phone 195C via a web browser interface using Hyper-Text Transport Protocol (HTTP), thus allowing clinical personnel to view the patient-specific alarm and physiological information and control alarm threshold settings as desired. Although illustrated as communicating with mobile devices 195, other devices, such as desktop computers, may also interact with the platform 100 using a similar interface. Although described above as a web-based interface, implementations may use non-web user interfaces for delivery and display of clinical information. An example of such a platform 100 is the Sickbay™ platform from Medical Informatics Corp. of Houston, Tex. (SICKBAY is a trademark of Medical Informatics Corp.)

Figure 2:
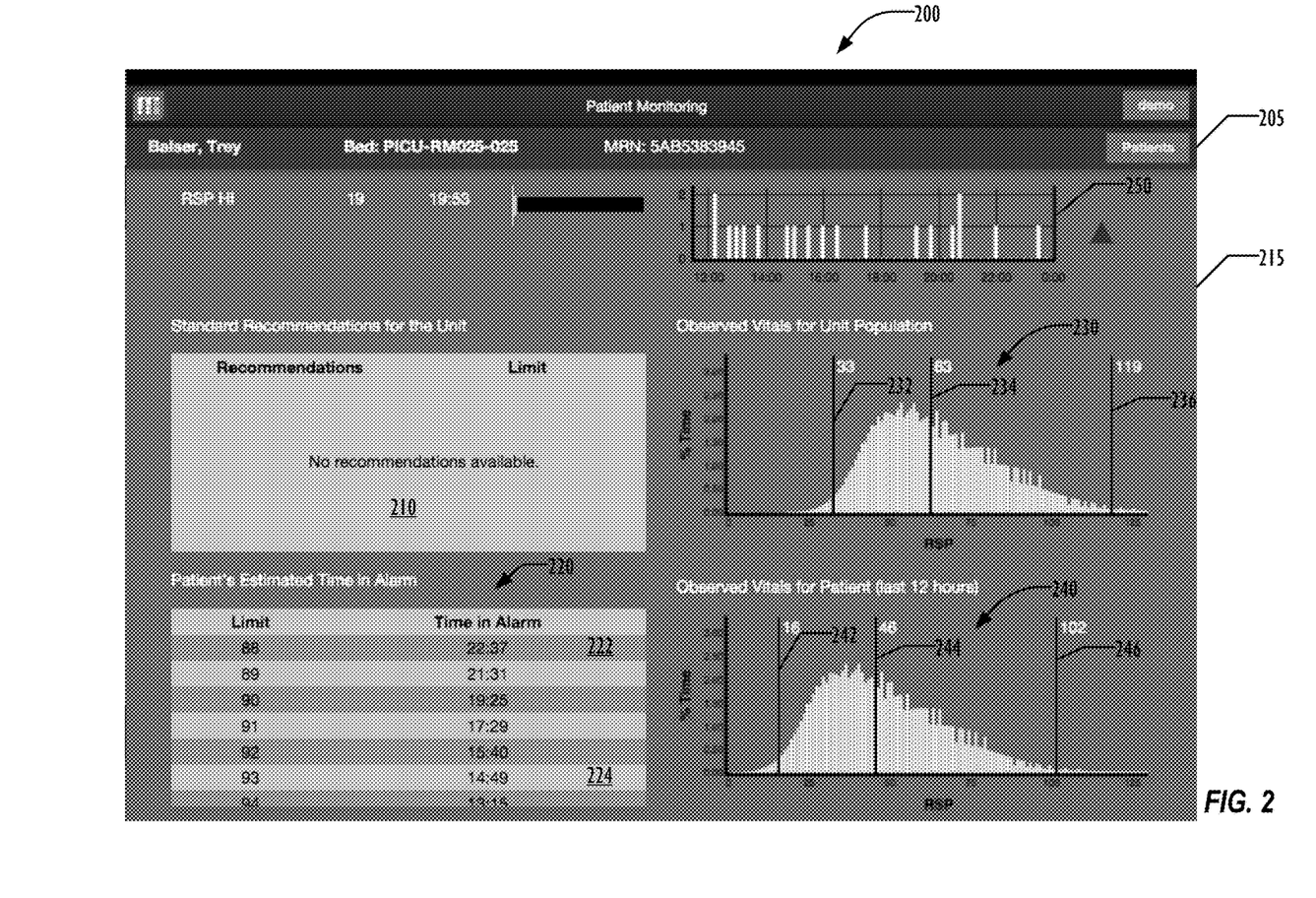
FIGS. 2-3 are screenshots illustrating a patient-specific alarm monitoring tool according to one embodiment.
Figure 3:
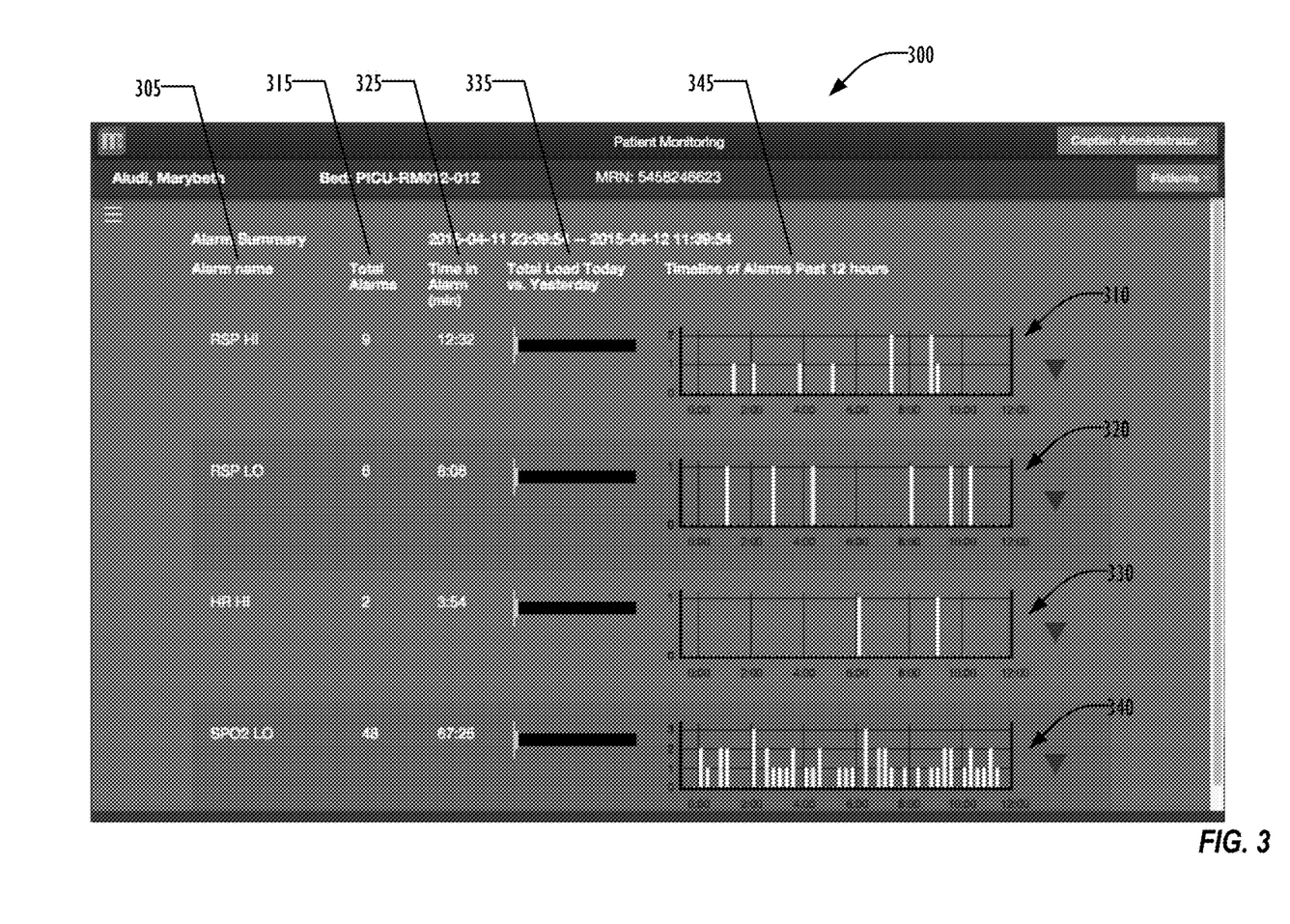

FIG. 2 is a screenshot of a display showing a user interface for displaying alarm and physiological data for a patient according to one embodiment. (All patient data displayed in FIGS. 2-3 is fictitious and no individually identifiable health information is included in the figures.) As illustrated, patient monitoring display 200, which may be displayed in a web-based or other user interface, provides an area for identifying information about the patient (205) and an area displaying alarm and physiological data for that patient (215). The format of the patient identification area 205 is illustrative and by way of example only, and any desired format may be used to display any patient identifying information as desired. Although the data illustrated in FIG. 2 is respiratory data, the person of skill in the art will recognize that other types of physiological data and alarms can be represented in this user interface.

Area 215 in this example is configured for displaying information related to high respiratory rate (RSP HI) alarms. Similar displays may be provided for other vital signs, such as $SpO_2$ (arterial oxygen saturation). The Patient Alarm Data Application can automatically adjust the data displayed and calculated for that individual patient based on patient-specific factors such as age, diagnosis, treatment, or bed location (i.e. unit).

The Patient Alarm Data Application can display a patient's recent alarm history for an arbitrary time period, typically a 12 or 24-hour interval. The most recent interval is defined as the "current time period" (i.e., for a 12-hour interval, the most recent interval is the 12 hours from the present time). The interval before the current time period is defined as the "previous time period" (i.e., for a 12-hour interval, the previous time period is the 12 h ours from 12 hours ago). This can include calculated metrics related to that alarm history such as total number of alarms or time in alarm. The arrangement of elements in FIG. 2 is illustrative and by way of example only, and other elements and arrangements of elements may be included in various embodiments.

The data displayed in the user interface of area 215 is generally patient-specific, although unit population data may be displayed for comparison purposes in some embodiments. For example, as illustrated in FIG. 2, a histogram 230 displays a graphical representation of RSP data for the unit population, i.e., the population at the facility corresponding to the patient, for visual comparison with RSP data observed for the patient identified in area 205. In one embodiment, the unit population graphical representation can be sensitive to the patient's state, such as an age-matched or condition-matched unit population. Percentile markers 232, 234, and 236 may be provided to indicate 1% of the data (232), 50% of the data (234), and 99% of the data (236) or any other desired breakpoints in the data. In this example, the histogram 230 shows the respiration rate on the x-axis and percentage of time on the y-axis. In some embodiments, the unit population graphical representation may be selectable between various unit populations. For example, the unit population graphical representation may initially be an entire unit population, but may be switchable between that and an age-matched population or a diagnosis-matched population, providing the clinical personnel with multiple population baselines to compare against the patient-specific vital signs data of histogram 240. In another example, population baseline data illustrated in the histogram 230 may be configurable, and may include baseline data from outside the clinical facility if desired and available. The display can provide insight to clinical personnel that would be unavailable merely looking at patent real-time monitor data, including detection of situations that may go on for extended periods that may have significant deleterious effect on the patient. For example, conventional monitoring techniques cannot show how long a patient has been outside of an alarm limit.

Similarly the patient specific RSP data is shown is the histogram 240, with corresponding percentile markers 242 (1%), 244 (50%), and 246 (99%). By placing the histograms 230 and 240 adjacent to each other, clinical personnel viewing the display 200 can easily see that the patient has a skewed respiration rate profile.

Both histograms 230 and 240 as illustrated are based on a 12-hour current time period. Embodiments may allow clinical personnel to select alternate time periods, such as a 24-hour current time period, and may allow switching between time periods, such as switching between 12 and 24-hour time periods. Although presented as a histogram in FIG. 2, the physiological data may use other types of graphical representations as desired.

In one embodiment, instead of or in addition to comparing the patient vitals for the current time period to the corresponding vitals of a unit populations, the display 200 may compare current time period data with previous time period data for the patient.

The Patient Alarm Data Application can also display the standard alarm limits, default device limit settings, policy limits, and delays for the patient's hospital unit (NICU, CVICU, PCU, etc.) in the area 210. Although in FIG. 2 no recommendations are available for display, recommendation may be provided as standard alarm thresholds, such as a recommendation for "A limit for SpO$_2$" and a corresponding value, such as "90."

Having a timeline of recent alarms as illustrated in area 250 is useful for clinical personnel, but gives the clinical personnel no guidance to help the clinical personnel determine proper settings for the alarm threshold. Thus area 220 provides calculated information on the effect of setting a proper alarm threshold value, by giving a table of threshold ("limit") values and an estimated time this patient would have been in alarm if that threshold were in place. Thus in line 222, a limit value of 88 for respiration would have caused this patient to be in alarm 22 minutes and 37 second, while as indicated in line 224 a higher limit value of 93 would have caused this patient to be in alarm nearly 8 minutes less over the 12 hour period illustrated in FIG. 2. In one embodiment, another estimated value may be provided, indicating an estimated change in the time in alarm, assuming the next time period is similar to the current time period. Although presented as a table 220, other presentation formats can be provided as desired, including a graphical representation of the alarm estimate information, such as a bar chart. Although as illustrated in FIG. 2 the area 220 indicates the estimated effect of a change in an alarm threshold, similar displays may be provided showing the effect of changing a delay value for an alarm.

Thus, the Patient Alarm Data Application can calculate and display recommended safe alarm limit settings, allowing a clinician or a clinical care team to make a better-informed decision on whether to adjust alarm threshold limits and if so, by how much.

The Patient Alarm Data Application is primarily a Clinician's or clinical care team tool, allowing clinicians to understand: 1) the way in which a patient's alarms are occurring, 2) identifying rapidly if alarm limits should be adjusted for that individual patient, 3) providing patient-specific information on the patient's baseline vitals, and 4) presenting the estimated impact of alarm limit and delay changes on the alarm load.

The distribution data about the alarm load provides a clinician more than what a clinician viewing a patient monitor could see, because the data provided is historical, aggregated and presented in a novel way. As each patient is admitted to the facility or unit, a record is established for that patient, to allow data to be captured and stored as soon as the patient is connected to the patient monitoring sensors.

The Patient Alarm Data Application can be automatically assigned and instantiated to new patients when they enter a unit. Alternately, the Patient Alarm Data Application may be instantiated based on a rule or manually upon a selection by clinical personnel.

Multiple sets of alarm profiles are available for different types of patient conditions. Alarms that a specific patient is capable of generating including alarms from ancillary devices or other hospital systems such as nurse call can be captured by the Sickbay Platform. Alarm profiles can be selected or automatically assigned for display by the Patient Alarm Data Application based on data collected by the system.

FIG. 3 is a screenshot 300 of an alternate profile for displaying alarm information for a patient. In this example, the display is a multi-vital sign display, providing alarm information for high respiratory rate (310), low respiratory rate (320), high heart rate (330), and low SpO$_2$ (340) alarms. The choice of alarms to include on the display is illustrative and by way of example only, and other alarms may be displayed in the user interface of FIG. 3. The choice of alarms may be configurable by the clinical personnel or in some embodiments may be automatically selected by the Patient Alarm Data Application, based on analysis of current time period data for the specific patient. As illustrated in FIG. 3, in addition to the timelines (345) showing how many times that particular alarm occurred during a time interval, other columns indicate the alarm name (305), the total number of alarms during the displayed time period (315), the time spent in alarm (325), and a comparison of a total alarm load today vs. yesterday (335). The alarm load data indicator 335 in one embodiment is shown as a bar, but in other embodiments may employ arrows or other indications of how the load has changed. Various embodiments may include additional columns or omit some of the columns displayed in FIG. 3. In one embodiment, the display of FIG. 3 can be treated as an alarm menu, such that selecting one of the rows 310, 320, 330, or 340 of FIG. 3 may cause the Patient Alarm Data Application to display the alarm-specific display of FIG. 2.

Figure 4:
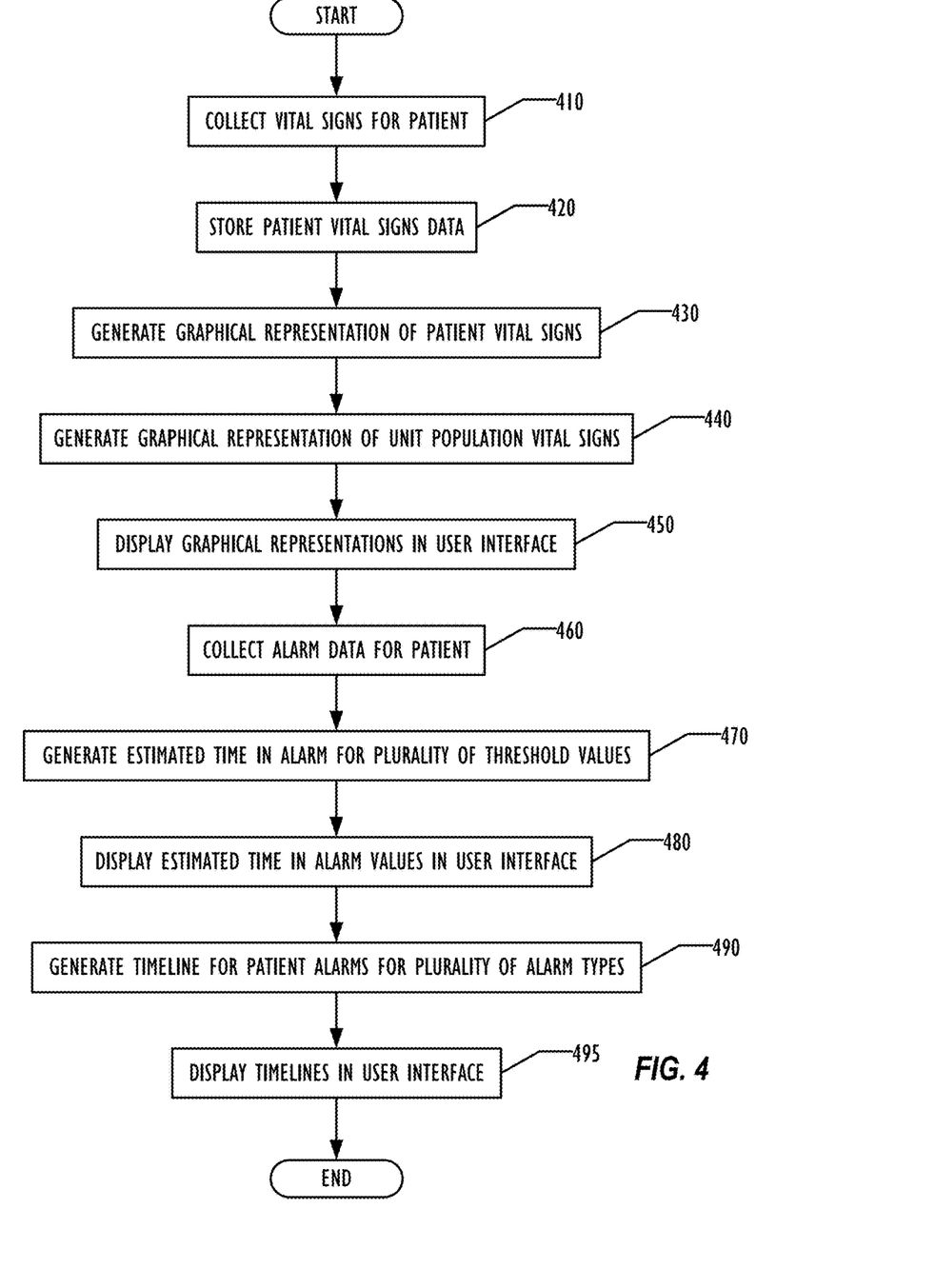
FIG. 4 is a flowchart illustrating a technique for displaying patient-specific alarms and vital signs data according to one embodiment.

FIG. 4 is a flowchart illustrating an algorithm for processing alarm and vital signs data for patient-specific alarm monitoring according to one embodiment. In block 410, the system collects physiological data (vital signs) for the patient, generating baseline patient data that is stored in block 420. In blocks 430 and 440, the patient alarm data application generates graphical representations of the patient vital signs data and the unit population vital signs data such as is displayed in FIG. 2. Those graphical representations may then be displayed in the user interface in block 450. In addition, in block 460 alarm data for the patient is collected. In some embodiments, this may include identifying data about specific alarm setting values, either automatically, or in response to user input. In such embodiments, the timelines such as are illustrated in FIGS. 2 and 3 may also include markers or indicators that indicate when an alarm threshold value was changed, the previous alarm threshold value, and/or the new alarm threshold value and other relevant data as desired.

In block 470, the Patient Alarm Data Application may generate the estimated time in alarm for a plurality of threshold values. These threshold values may be a range of threshold values, such as are illustrated in FIG. 2, or may be a configured set of specific threshold values to consider. Either the range or configured set may be determined by a user selection or in some embodiments may be established by a rule.

In block 480, the Patient Alarm Data Application may display the estimated time in alarm values in the user interface for the plurality of threshold values, as illustrated in area 220 of FIG. 2. In some embodiments, a tabular display as illustrated in FIG. 2 may be used; in other embodiments a graphical representation may be used as desired. In block 490, the plurality of timelines and other alarm-related data may be generated and displayed in block 495 as illustrated in FIG. 3.

Figure 5:
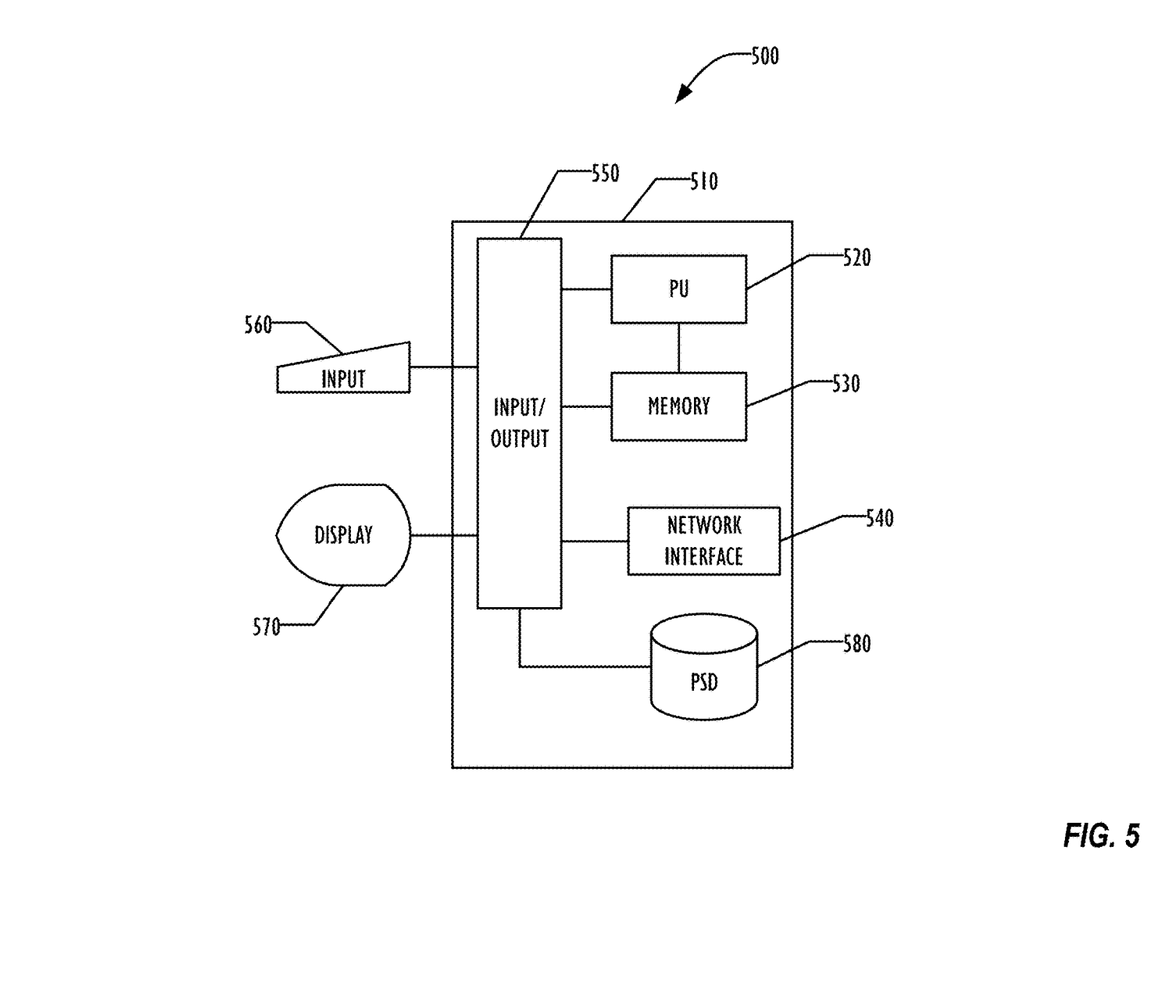
FIG. 5 is a block diagram illustrating a computer system for use with a patient alarm monitoring tool according to one embodiment.

Referring now to FIG. 5, an example computer 500 for use as one of the servers 180-190 is illustrated in block diagram form. Example computer 500 comprises a system unit 510 which may be optionally connected to an input device or system 560 (e.g., keyboard, mouse, touch screen, etc.) and display 570. A program storage device (PSD) 580 (sometimes referred to as a hard disc) is included with the system unit 510. Also included with system unit 510 is a network interface 540 for communication via a network with other computing and corporate infrastructure devices (not shown). Network interface 540 may be included within system unit 510 or be external to system unit 510. In either case, system unit 510 will be communicatively coupled to network interface 540. Program storage device 580 represents any form of non-volatile storage including, but not limited to, all forms of optical and magnetic, including solid-state, storage elements, including removable media, and may be included within system unit 510 or be external to system unit 510. Program storage device 580 may be used for storage of software to control system unit 510, data for use by the computer 500, or both.

System unit 510 may be programmed to perform methods in accordance with this disclosure (an example of which is in FIG. 4). System unit 510 comprises a processor unit (PU) 520, input-output (I/O) interface 550 and memory 530. Processing unit 520 may include any programmable controller device, such as microprocessors available from Intel Corp. and other manufacturers. Memory 530 may include one or more memory modules and comprise random access memory (RAM), read only memory (ROM), programmable read only memory (PROM), programmable read-write memory, and solid-state memory, which may store instructions that when executed cause the processor unit to perform the actions described above. These instructions may be loaded into memory from the program storage device 580. One of ordinary skill in the art will also recognize that PU 520 may also include some internal memory including, for example, cache memory.

Conventional monitoring systems have not been able to provide such patient-specific alarm and vital signs reporting or predictive information on the effects of changes in alarm settings for the specific patient. In contrast, novel feature of embodiments of the Patient Alarm Data Application may include one or more of:

Display of historical patient-specific alarms and alarm trends

Display of an alarm menu as pathway for viewing greater alarm data and patient data details Display of a specific patient's specific alarm data: Total Alarms in period; Time in Alarm; Total Load Today vs. Yesterday (compare current time period to previous time period); Timeline of Alarms for Past (24-hour) Period (timeline for current time period).

Display of a specific patient's specific alarm data: Standard Recommended for that unit of the hospital.

Display of a specific patient's specific alarm data: Observed Vitals (for a specific alarm) for Unit Population.

Display of a specific patient's specific alarm data: Patient Specific recommendations table of possible settings with predicted % Time in Alarm and Estimated % Change.

Display of a specific patient's specific alarm data: Histogram of Observed Vitals with mean and percentiles marked.

The Patient Alarm Data Application allows clinicians to understand and manage their patients' alarm settings better. The Patient Alarm Data Application allows clinicians to enforce policy or track policy variations by clinicians. The Patient Alarm Data Application allows clinicians to rapidly determine if an alarm or set of alarms have been chattering or otherwise non-critical, and then guide the clinical personnel toward a better alarm setting, based on predictions of estimated time in alarm for possible new alarm settings. Clinical personnel may be able to modify a treatment plan because of the insight gained by being able to view the alarm and vital signs data as displayed in the user interface described above.

While certain exemplary embodiments have been described in details and shown in the accompanying drawings, it is to be understood that such embodiments are merely illustrative of and not devised without departing from the basic scope thereof, which is determined by the claims that follow.

We claim:

1. A method of managing alarms in a clinical environment, comprising:
    receiving physiological data of a physiological data type for each patient of a population of a clinical unit
    aggregating the physiological data for the population of the clinical unit as a whole into an aggregated physiological data;
    receiving a selection of a patient of the population of the clinical unit
    displaying the physiological data for the patient and the aggregated physiological data
    in a patient-specific user interface; and
    calculating a plurality of time in alarm duration estimates for the patient for a plurality of alarm threshold values; and
    displaying in the patient-specific user interface a graphical representation of the plurality of time in alarm duration estimates as a function of alarm threshold value.

2. The method of claim 1, further comprising:
displaying in the patient-specific user interface a total number of alarms for the patient and total time in alarm duration for the patient corresponding to the physiological data type.

3. The method of claim 1, further comprising:
displaying in the patient-specific user interface a plurality of timelines of alarms for the patient corresponding to a plurality of physiological data types during the predetermined time interval.

4. The method of claim 1, further comprising:
receiving a user selection of the timeline of alarms; and
displaying the graphical representation of the plurality of time in alarm duration estimates responsive to the user selection of the timeline of alarms.

5. The method of claim 1, further comprising:
identifying a current alarm threshold for the physiological data type;
displaying the current alarm threshold in the patient-specific user interface; and
displaying alarm threshold changes in the patient-specific user interface.

6. The method of claim 1, further comprising:
instantiating the patient-specific user interface automatically responsive to a clinical environment policy.

7. The method of claim 1, wherein the plurality of alarm threshold values comprises a range of threshold values.

8. A non-transitory machine readable medium, on which are stored instructions, comprising instructions that when executed cause a clinical patient monitoring computer to:
receive physiological data of a physiological data type for each patient of a population of a clinical unit;
aggregate the physiological data for the population of the clinical unit as a whole into an aggregated physiological data;
receive a selection of a patient of the population of the clinical unit;
display the physiological data for the patient and the aggregated physiological data
in a patient-specific user interface; and
calculate a plurality of time in alarm duration estimates for the patient for a plurality of alarm threshold values; and
display in the patient-specific user interface a graphical representation of the plurality of time in alarm duration estimates as a function of alarm threshold value.

9. The machine readable medium of claim 8, wherein the instructions further comprise instructions that when executed cause the clinical patient monitoring computer to:
display in the patient-specific user interface a total number of alarms for the patient and total time duration in alarm for the patient corresponding to the physiological data type.

10. The machine readable medium of claim 8, wherein the instructions further comprise instructions that when executed cause the clinical patient monitoring computer to:
display in the patient-specific user interface a plurality of timelines of alarms for the patient corresponding to a plurality of physiological data types during the predetermined time interval.

11. The machine readable medium of claim 8, wherein the instructions further comprise instructions that when executed cause the clinical patient monitoring computer to:
identify a current alarm threshold for the physiological data type;
display the current alarm threshold in the patient-specific user interface; and
display alarm threshold changes in the patient-specific user interface.

12. The machine readable medium of claim 8, wherein the instructions further comprise instructions that when executed cause the clinical patient monitoring computer to:
instantiate the patient-specific user interface automatically responsive to a clinical environment policy.

13. The machine readable medium of claim 8, wherein the instructions further comprise instructions that when executed cause the clinical patient monitoring computer to:
receive a selection of a timeline of alarms of the plurality of timelines of alarms; and
display the graphical representation of the time in alarm duration estimates responsive to the selection of the timeline of alarms.

14. The machine readable medium of claim 8, wherein the plurality of alarm threshold values comprises a range of alarm threshold values.

15. A clinical patient monitor, comprising:
one or more processors;
a memory, on which are stored instructions, comprising instructions that when executed cause at least some of the one or more processors to:
receive physiological data of a physiological data type for each patient of a population of a clinical unit;
aggregate the physiological data for the population of the clinical unit as a whole into an aggregated physiological data;
receive a selection of a patient of the population of the clinical unit;
display the physiological data for the patient and the aggregated physiological data in a patient-specific user interface; and
calculate a plurality of time in alarm duration estimates for the patient for a plurality of alarm threshold values; and
display in the patient-specific user interface a
graphical representation of the plurality of time in alarm
duration estimates as a function of alarm threshold value.

16. The clinical patient monitor of claim 15, wherein the instructions further comprise instructions that when executed cause at least some of the one or more processors to:
display in the patient-specific user interface a plurality of timelines of alarms for the patient corresponding to a plurality of physiological data types during the predetermined time interval.

17. The clinical patient monitor of claim 15, wherein the instructions further comprise instructions that when executed cause at least some of the one or more processors to:
identify a current alarm threshold for the physiological data type;
display the current alarm threshold in the patient-specific user interface; and
display alarm threshold changes in the patient-specific user interface.

18. The clinical patient monitor of claim 15, wherein the instructions further comprise instructions that when executed cause at least some of the one or more processors to:
instantiate the patient-specific user interface automatically responsive to a clinical environment policy.

19. The clinical patient monitor of claim 15, wherein the plurality of alarm threshold values comprises a range of alarm threshold values.

20. The clinical patient monitor of claim 15, wherein the instructions further comprise instructions that when executed cause at least some of the one or more processors to:
   receive a selection of a timeline of alarms of the plurality of timelines of alarms; and
   display the graphical representation of the time in alarm duration estimates responsive to the user selection of the timeline of alarms.

* * * * *